United States Patent
Lv et al.

(10) Patent No.: US 11,939,277 B2
(45) Date of Patent: Mar. 26, 2024

(54) CONTINUOUS PREPARATION METHOD OF 2,3,3,3-TETRAFLUOROPROPENE

(71) Applicant: Zhejiang Juhua Technology Center Co., Ltd., Zhejiang (CN)

(72) Inventors: Yang Lv, Zhejiang (CN); Hongfeng Li, Zhejiang (CN); Qi Jiang, Zhejiang (CN); Liyong Ma, Zhejiang (CN); Jinming Wang, Zhejiang (CN)

(73) Assignee: Zhejiang Juhua Technology Center Co., Ltd., Zhejiang (CN)

( * ) Notice: Subject to any disclaimer, the term of this patent is extended or adjusted under 35 U.S.C. 154(b) by 431 days.

(21) Appl. No.: 17/419,298

(22) PCT Filed: Dec. 17, 2019

(86) PCT No.: PCT/CN2019/000248
§ 371 (c)(1),
(2) Date: Jun. 29, 2021

(87) PCT Pub. No.: WO2020/133554
PCT Pub. Date: Jul. 2, 2020

(65) Prior Publication Data
US 2022/0081379 A1    Mar. 17, 2022

(30) Foreign Application Priority Data

Dec. 29, 2018   (CN) .......................... 201811635397.6

(51) Int. Cl.
*C07C 17/20* (2006.01)
*B01D 61/02* (2006.01)
(Continued)

(52) U.S. Cl.
CPC .......... *C07C 17/206* (2013.01); *B01D 61/027* (2013.01); *B01D 67/0011* (2013.01);
(Continued)

(58) Field of Classification Search
CPC ..... C07C 17/206; C07C 17/275; C07C 17/04; C07C 17/25; C07C 17/38; C07C 21/04; C07C 21/18; C07C 19/01
See application file for complete search history.

(56) References Cited

U.S. PATENT DOCUMENTS

2009/0240090 A1    9/2009   Merkel et al.

FOREIGN PATENT DOCUMENTS

| CN | 102199071 | 5/2013 |
| CN | 105026346 | 11/2015 |

(Continued)

*Primary Examiner* — Jafar F Parsa
(74) *Attorney, Agent, or Firm* — JCIP GLOBAL INC.

(57) ABSTRACT

The invention provides a continuous preparation method of 2,3,3,3-tetrafluoropropene, comprising the following steps: carrying out liquid-phase catalytic telomerization reaction on ethylene and carbon tetrachloride serving as initial raw materials in the presence of a composite catalyst to obtain a reaction product; performing two-stage membrane separation and purification on the reaction product, and then sequentially performing a primary high-temperature cracking reaction, a gas-phase chlorination reaction, a secondary high-temperature cracking reaction, a primary gas-phase catalytic fluorination reaction and a secondary gas-phase catalytic fluorination reaction to obtain a reaction product; condensing and rectifying the secondary gas-phase catalytic fluorination reaction product to obtain the 2,3,3,3-tetrafluoropropene product.

10 Claims, 1 Drawing Sheet

(51) Int. Cl.
  *B01D 67/00*   (2006.01)
  *B01D 69/12*   (2006.01)
  *B01D 71/02*   (2006.01)
  *B01D 71/34*   (2006.01)
  *B01D 71/64*   (2006.01)
  *B01D 71/68*   (2006.01)
  *B01J 23/26*   (2006.01)
  *B01J 23/745*  (2006.01)
  *B01J 31/02*   (2006.01)

(52) U.S. Cl.
  CPC ..... *B01D 67/0016* (2013.01); *B01D 67/0093* (2013.01); *B01D 69/12* (2013.01); *B01D 71/021* (2013.01); *B01D 71/34* (2013.01); *B01D 71/64* (2013.01); *B01D 71/68* (2013.01); *B01J 23/26* (2013.01); *B01J 23/745* (2013.01); *B01J 31/0258* (2013.01); *B01J 2231/20* (2013.01)

(56) References Cited

FOREIGN PATENT DOCUMENTS

| CN | 107074697 | 8/2017 | |
|---|---|---|---|
| CN | 109796300 | 5/2019 | |
| WO | 2009015317 | 1/2009 | |
| WO | WO-2009125201 A2 * | 10/2009 | ............ C07C 17/04 |
| WO | 2017178857 | 10/2017 | |

* cited by examiner

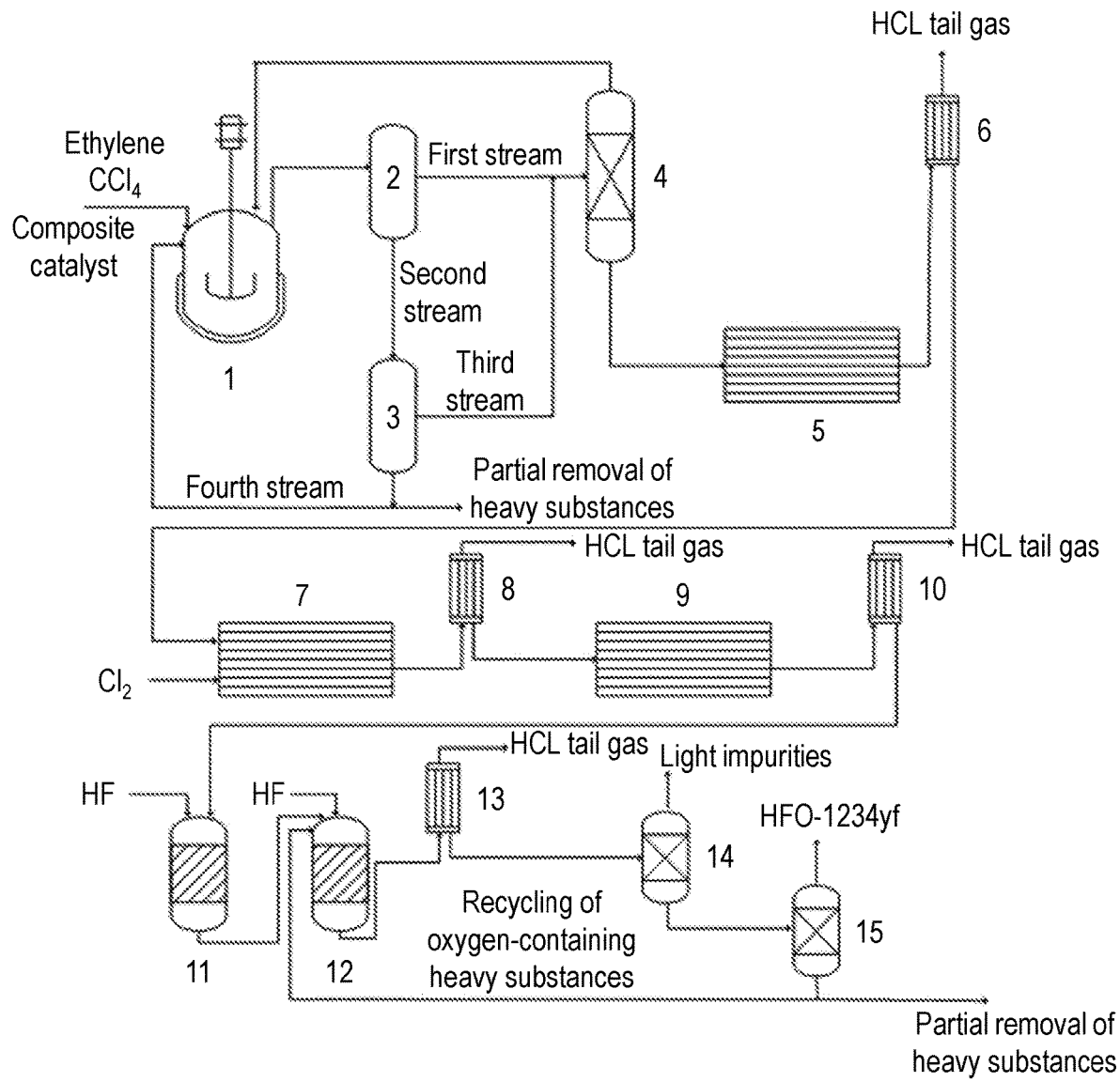

CONTINUOUS PREPARATION METHOD OF 2,3,3,3-TETRAFLUOROPROPENE

CROSS-REFERENCE TO RELATED APPLICATION

This application is a 371 of international application of PCT application serial no. PCT/CN2019/000248, filed on Dec. 17, 2019, which claims the priority benefit of China application no. 201811635397.6, filed on Dec. 29, 2018. The entirety of each of the above mentioned patent applications is hereby incorporated by reference herein and made a part of this specification.

BACKGROUND

Technical Field

The present disclosure relates to a preparation method of fluorine-containing olefins, in particular to a continuous preparation method of 2,3,3,3-tetrafluoropropene.

Description of Related Art

With the increasingly severe global warming situation, new fluorine refrigerant alternatives have become a global hot topic. Hydrofluoroolefin 2,3,3,3-tetrafluoropropene (HFO-1234yf), as a refrigerant containing a single working fluid, has excellent environmental parameters, such as GWP=4, ODP=0, its LCCP (Life Cycle Climate Performance) is lower than that of HFC-134a, and its system performance is better than that of HFC-134a. More importantly, HFO-1234yf, as a new generation refrigerant, can be used in automotive MAC systems, and automotive manufacturers do not need to replace vehicle-mounted systems. HFO-1234yf is considered to be the best substitute for a new generation of automotive refrigerants, and its application scope is gradually being widened.

Many preparation routes of 2,3,3,3-tetrafluoropropene have been disclosed at present. Among them, the routes with industrial practical value mainly include: firstly synthesizing 2-chloro-3,3,3-trifluoropropene (HCFO-1233xf), and then converting HCFO-1233xf into 2-chloro-1,1,1,2-tetrafluoropropane (HCFC-244bb) by a liquid phase method or a gas phase method, and then carrying out gas-phase catalytic fluorination to obtain HFO-1234yf. The intermediate product 2-chloro-3,3,3-trifluoropropene can be produced by fluorinating 1,1,1,2,3-pentachloropropane; or can be prepared from ethylene and carbon tetrachloride by telomerization, liquid-phase chlorination, fluorination, and other processes.

For example, US2009/0240090 describes a method where HCFO-1233xf is prepared by fluorinating 1,1,1,2,3-pentachloropropane in the absence of oxygen, and then converted into HCFC-244bb by a liquid-phase method and then gas-phase catalytic fluorination is carried out to prepare HFO-1234yf. For this process, more steps are involved, raw materials are not easy to obtain, and the last step of catalytic fluorination is carried out at a temperature high up to 460° C., which causes an adverse effect on the property stability of the catalyst and shortens the service life of the catalyst.

Another example is WO2009/015317 which describes a method where a raw material, a chloride such as 1,1,2,3-tetrachloropropene (TCP), 1,1,1,2,3-pentachloropropane (HCC-240db) or 2,3,3,3-tetrachloropropene (HCO-1230xf) undergoes catalytic fluorination with HF to obtain HCFO-1233xf and then HCFO-1233xf is fluorinated to obtain HFO-1234yf. The catalyst in this method can only run continuously for 67 hours, and its service life is not significantly improved after the addition of a stabilizer.

For example, CN102199071B describes a method where raw materials ethylene and carbon tetrachloride are subjected to telomerization and liquid-phase chlorination (catalyzed by ferric chloride) in the presence of a composite metal (serving as a catalyst) and DMF (serving as a co-catalyst), and then fluorination is carried out with HF in the presence of a catalyst $CrF_3$ to produce 2-chloro-3,3,3-trifluoropropene, and finally gas-phase catalytic fluorine-chlorine exchange is carried out in the presence of a catalyst $SbF_5$/porous aluminum fluoride to obtain HFO-1234yf. This method involves two liquid phase process steps. The catalysts and co-catalysts used are directly discharged without being recovered, and the amount of "three wastes" is relatively large. Secondly, the selectivity of HFO-1234yf is not high, and the life of the gas-phase fluorination catalyst used is unknown.

CN105026346A describes an improved method for preparing 1,1,2,3-tetrachloropropene using ethylene and carbon tetrachloride as raw materials. Although this method uses flash evaporation to recover part of the catalysts and auxiliaries, the temperature of a reboiler is in a range of 95° C. to 105° C. and the energy consumption is relatively high.

SUMMARY

To solve the defects of the prior art, the present disclosure provides a continuous preparation method of 2,3,3,3-tetrafluoropropene with high production efficiency, good environmental friendliness, and low cost.

In order to solve the above technical problem, the technical solution adopted in the present disclosure is as follows: a continuous preparation method of 2,3,3,3-tetrafluoropropene, including the following steps:

(1) in the presence of a composite catalyst, continuously introducing ethylene and carbon tetrachloride into a telomerization reactor for liquid-phase catalytic telomerization reaction to obtain a first reaction product, wherein the reaction is carried out at a temperature of 90° C. to 120° C., under a pressure of 0.5 Mpa to 1.0 Mpa and with a residence time of 1 h to 2 h, a molar ratio of carbon tetrachloride to ethylene is (1-4):1, and a mass ratio of carbon tetrachloride to composite catalyst is (40-100):1;

(2) introducing the first reaction product obtained in step (1) into a first membrane separator for separation to obtain a first stream and a second stream;

(3) introducing the second stream obtained in step (2) into a second membrane separator for separation to obtain a third stream and a fourth stream, and recycling the fourth stream to the telomerization reactor;

(4) mixing the third stream obtained in step (3) with the first stream obtained in step (2), and then introducing the mixture into a first separation column to obtain an overhead fraction of the first separation column and a bottom component of the first separation column, and recycling the overhead fraction of the first separation column to the telomerization reactor;

(5) carrying out high-temperature cracking and condensing on the bottom component of the first separation column obtained in step (4) to obtain a second reaction product, wherein the cracking is carried out at a temperature of 350° C. to 500° C., and the residence time is within a range of 1 s to 8 s;

(6) carrying out gas-phase chlorination and condensing on the second reaction product obtained in step (5) in the presence of chlorine gas to obtain a third reaction product, wherein the gas-phase chlorination is carried out at a temperature of 140° C. to 170° C., the residence time is within a range of 0.5 s to 5.5 s, and a molar ratio of the chlorine gas to the second reaction product is within a range of (1-4):1;

(7) carrying out high-temperature cracking and condensing on the third reaction product obtained in step (6) to obtain a fourth reaction product, wherein the cracking is carried out at a temperature of 350° C. to 500° C., and the residence time is within a range of 2 s to 15 s;

(8) in the presence of a first fluorination catalyst, introducing the fourth reaction product obtained in step (7) and hydrogen fluoride into a first catalytic reactor for gas-phase catalytic fluorination reaction to obtain a fifth reaction product, wherein the reaction is carried out at a temperature of 250° C. to 300° C., under a pressure of 0.5 Mpa to 1.5 Mpa, with a contact time of 1 s to 25 s, and a molar ratio of the HF to the fourth reaction product is within a range of (5-25):1; and (9) in the presence of a second fluorination catalyst, introducing the fifth reaction product obtained in step (8) and hydrogen fluoride into a second catalytic reactor for gas-phase catalytic fluorination reaction, wherein the reaction is carried out at a temperature of 250° C. to 330° C., under a pressure of 0.8 Mpa to 1.2 Mpa, with a contact time of 5 s to 35 s, and a molar ratio of the HF to the fifth reaction product is within a range of (5-30):1; and condensing and rectifying the reaction product to obtain chlorine-containing column bottom liquid and a 2,3,3,3-tetrafluoropropene product.

The composite catalyst in step (1) of the present disclosure includes a catalyst and a co-catalyst, and preferably includes, by weight, 0.5 to 1 part of the catalyst and 0.5 to 1 part of the co-catalyst. The catalyst includes preferably one or more of iron powder, iron wires, ferric chloride, and ferrous chloride, more preferably iron powder. A particle size of the iron powder is preferably less than 200 meshes, so that the iron powder can be mixed with carbon tetrachloride to form a slurry, and continuously enter the telomerization reactor. In the present disclosure, an alkyl phosphate can be used as the co-catalyst, and the co-catalyst is preferably triethyl phosphate (TEP) or tributyl phosphate (TBP). The co-catalyst can be mixed with carbon tetrachloride according to a certain ratio to prepare a mixed liquid before the reaction starts, and the co-catalyst and the carbon tetrachloride are continuously introduced into the telomerization reactor together.

The first fluorination catalyst in step (8) of the present disclosure can be prepared by a co-mixing method or a co-precipitation method known in the art. For example, neodymium chloride and chromium chloride can be dissolved in water in a certain proportion, and then reacted with a precipitating agent, the pH of the reaction solution is then adjusted to alkaline, the reaction solution is stirred, precipitated, filtered, dried at a temperature of 120° C. to 150° C., and then calcined at 380° C., thus obtaining a catalyst precursor. Before the reaction, the pelletized catalyst precursor is loaded into the first catalytic reactor, and then activated, before use, by anhydrous hydrogen fluoride (AHF) diluted with nitrogen to different concentrations. The first fluorination catalyst is preferably composed of, by weight, 5 to 25 parts of $Nd_2O_3$ and 75 to 95 parts of $Cr_2O_3$.

The second fluorination catalyst in step (9) of the present disclosure can be prepared by a co-mixing method or a co-precipitation method known in the art. For example, thulium chloride hydrate, dysprosium chloride, and chromium chloride can be dissolved in water in a certain proportion, and then the mixed solution reacts with a precipitating agent, the pH of the reaction solution is then adjusted to alkaline, the reaction solution is stirred, precipitated, filtered, dried at a temperature of 120° C. to 150° C., and then calcined at 420° C., thus obtaining a catalyst precursor. Before the reaction, the pelletized catalyst precursor is loaded into the second catalytic reactor, and then activated, before use, by anhydrous hydrogen fluoride (AHF) diluted with nitrogen to different concentrations. The second fluorination catalyst is preferably composed of, by weight, 5 to 15 parts of $Dy_2O_3$, 3 to 20 parts of $Tm_2O_3$, and 60 to 94 parts of $Cr_2O_3$.

The chlorine-containing column bottom liquid in step (9) of the present disclosure mainly includes heavy substances such as 3-chloro-2,3,3-trifluoropropene and 2-chloro-3,3,3-trifluoropropene. As a preferred embodiment of the present disclosure, the chlorine-containing column bottom liquid in step (9) can be recycled to the second catalytic reactor for further fluorination. In order to avoid accumulation of some chlorine-containing heavy column bottom liquid, part of the chlorine-containing heavy column bottom liquid can be removed regularly, and the removed materials can be subjected to intermittent rectification to further recover useful materials therefrom.

In the present disclosure, the first reaction product obtained in step (1) is a crude product of the reaction solution containing 1,1,1,3-tetrachloropropane (HCC-250fb), and membrane materials used for the subsequent two stages of membrane separation of the HCC-250fb crude product and their preparation methods are different. The membrane used in the first membrane separator is a composite nanofiltration membrane, the membrane performs separation on the basis of the dissolution-precipitation principle, and non-polar molecules can very easily permeate the membrane. The operating temperature of the first membrane separator is preferably within a range of 15° C. to 80° C., and the operating pressure of the first membrane separator is preferably within a range of 0.5 Mpa to 1.0 Mpa. The application form of the composite nanofiltration membrane used in the first membrane separator can be one of roll membrane, hollow fiber membrane, tubular membrane, and plate membrane, and a preparation method of the composite nanofiltration membrane includes the following steps:

(1) placing 0.25 to 1 part of carbon nanotubes by weight into 100 parts of solvent N,N-dimethylformamide by weight, and carrying out ultrasonic dispersion for 4 h to 6 h to obtain a mixed solution;

(2) placing 30 to 60 parts of polyvinylidene fluoride by weight and 18 to 40 parts of polyimide by weight into the mixed solution obtained in step (1), and stirring the solution for 10 to 20 hours to obtain a casting solution;

(3) resting the casting solution, obtained in step (2), at 25° C. to 30° C. for 24 h to 48 h to obtain a degassed casting solution;

(4) scraping the degassed casting solution obtained in step (3) at 10° C. to 20° C. to obtain a scraped casting solution; and (5) volatilizing the scraped casting solution obtained in step (4) in the air for 1 min to 5 min, placing the volatilized casting solution in deionized water so that the casting solution is coagulated into a membrane, taking out the formed membrane from the coagulating solution, and rinsing the membrane with deionized water, thus obtaining the composite nanofiltration membrane.

The membrane used in the second membrane separator of the present disclosure is a modified nanofiltration membrane. The membrane uses a polyethersulfone ultrafiltration membrane as a base membrane and performs separation depending on different molecular sizes, and the cutoff molecular weight of the membrane is greater than 150. The operating temperature of the second membrane separator is preferably 25° C. to 60° C., and the operating pressure of the first membrane separator is preferably 1.0 Mpa to 1.5 Mpa. The application form of the modified nanofiltration membrane used in the second membrane separator can be one of roll membrane, hollow fiber membrane, tubular membrane, and plate membrane, and a preparation method of the composite nanofiltration membrane includes the following steps:

(1) cleaning a polyethersulfone base membrane with deionized water, and soaking the polyethersulfone base membrane in deionized water for 8 h to 12 h, and changing the deionized water every 2 h, thus obtaining the soaked polyethersulfone base membrane;

(2) placing the soaked polyethersulfone base membrane, obtained in step (1), in a polyacrylic acid solution with a concentration of 0.05 mol/L to 0.1 mol/L, the polyacrylic acid solution immersing the polyethersulfone base membrane for 2 cm to 5 cm, and bubbling with $N_2$ for 0.5 h to 1 h to remove oxygen out of the solution; and (3) under the protection of nitrogen at room temperature, using a low-voltage mercury lamp with a power of 400 W to 800 W to irradiate the solution obtained in step (2) for 50 min to 120 min, and then taking out the membrane, and rinsing the membrane with deionized water, thus obtaining the modified nanofiltration membrane.

In the continuous preparation method of 2,3,3,3-tetrafluoropropene of the present disclosure, the first reaction product containing 1,1,1,3-tetrachloropropane (HCC-250fb) obtained in step (1) is subjected to two stages of different membrane separations, and the composite catalyst can be recycled. Secondly, the intermediate products obtained in the reaction process do not need to be purified, and the reactions can be carried out in sequence. Finally, the crude HFO-1234yf is purified to obtain a high-purity product. This method has significant market application prospects. The process route adopted by the present disclosure is as follows:

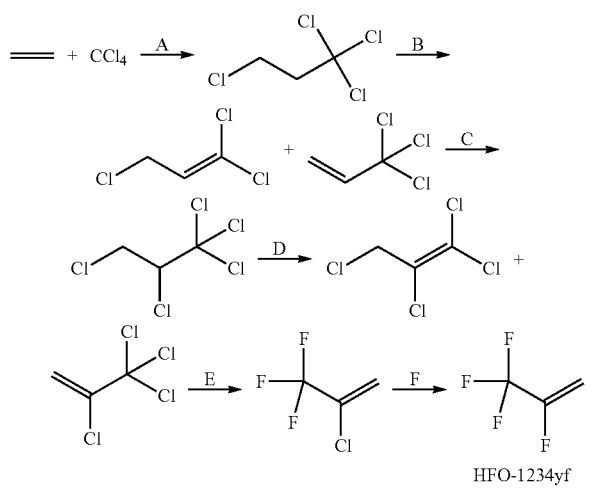

There is no limitation on the materials of all tubular reactors and catalytic reactors in the present disclosure. Any acid corrosion-resistant material can be used in the present disclosure, and Hastelloy, Inconel, and other commonly used corrosion-resistant materials are preferred. HCl, tail gas, and separated HF and $Cl_2$ in the present disclosure can be further recycled through a compressor.

Compared with the prior art, the advantages of the present disclosure are as follows:

1. The process is simple, and the continuous preparation of HFO-1234yf products is realized. The intermediate products of the reaction process do not need to be purified, the reactions can be carried out in sequence, the use of separation equipment is reduced, and the production process is greatly simplified.

2. Due to low cost, easy availability of raw materials, and reduced use of separation equipment, investment costs are significantly reduced. The liquid-phase catalytic telomerization reaction product is subjected to two stages of different membrane separations, and the composite catalyst can be recycled. The unreacted raw material carbon tetrachloride can be recycled, which further reduces the production cost.

3. The preparation method disclosed in the present disclosure is environmentally friendly, greatly simplifies the preparation process of HFO-1234yf, reduces the use of separation equipment, and lowers the energy consumption. Moreover, the recycling of incompletely fluorinated chlorine-containing heavy substances and composite catalyst significantly reduces the emissions of "three wastes".

BRIEF DESCRIPTION OF THE DRAWINGS

FIG. 1 is a process flow diagram of the present disclosure.
As shown in the FIGURE, 1—telomerization reactor, 2—first membrane separator, 3—second membrane separator, 4—first separation column, 5—first cracking reactor, 6—first condenser, 7—chlorination reactor, 8—second condenser, 9—second cracking reactor, 10—third condenser, 11—first catalytic reactor, 12—second catalytic reactor, and 13—fourth condenser, 14—second separation column, and 15—third separation column.

DESCRIPTION OF THE EMBODIMENTS

As shown in FIG. 1, the continuous preparation method of 2,3,3,3-tetrafluoropropene includes the following process:

(1) before the reaction starts, mixing a catalyst, a co-catalyst and carbon tetrachloride in a certain proportion to obtain a mixed solution, and continuously introducing the mixed solution through a constant flow pump into a telomerization reactor 1 equipped with a stirrer; at the same time, continuously introducing ethylene through the constant flow pump into the telomerization reactor 1 for liquid-phase catalytic telomerization reaction, and at the same time, carrying out constant-speed continuous draining at an outlet to maintain a system pressure to obtain a first reaction product;

(2) introducing the first reaction product into a first membrane separator 2 for separation to obtain a first stream and a second stream;

(3) introducing the second stream into a second membrane separator 3 for separation to obtain a third stream and a fourth stream, and recycling the fourth stream to the telomerization reactor 1, wherein in order to avoid the accumulation of heavy by-products such as 1,1,1,5-tetrachloropentane, the fourth stream can be partially removed continuously or periodically, and the removed materials can be subjected to intermittent rectification for further recovery of useful materials therefrom;

(4) mixing the third stream obtained in step (3) with the first stream obtained in step (2), and then introducing the mixture into a first separation column 4 to obtain an overhead fraction of the first separation column and a bottom component of the first separation column, wherein the overhead fraction of the first separation column is carbon tetrachloride through incomplete reaction, and recycling the overhead fraction of the first separation column to the telomerization reactor 1;

(5) introducing the bottom component of the first separation column into a first cracking reactor 5 for high-temperature cracking, and condensing cracking gas by a first condenser 6 to separate tail gas, thus obtaining a second reaction product;

(6) introducing the second reaction product and chlorine gas into a chlorination reactor 7 for gas-phase chlorination, and condensing the chlorination product by a second condenser 8 to separate HCl tail gas, thus obtaining a third reaction product;

(7) introducing the third reaction product into a second cracking reactor 9 for high-temperature cracking, and condensing cracking gas by a third condenser 10 to separate HCl tail gas, thus obtaining a fourth reaction product;

(8) introducing the fourth reaction product and hydrogen fluoride into a first catalytic reactor 11 filled with a first fluorination catalyst for gas-phase catalytic fluorination reaction, thus obtaining a fifth reaction product; and (9) introducing the fifth reaction product and hydrogen fluoride into a second catalytic reactor 12 filled with a second fluorination catalyst for gas-phase catalytic fluorination reaction; condensing the reaction product by a fourth condenser 13 to separate tail gas and then carrying out pressurized rectification via a second separation column 14 and a third separation column 15 to obtain the target product 2,3,3,3-tetrafluoropropene, wherein a small amount of light impurities obtained in the second separation column 14 can be recycled, and chlorine-containing heavy (mainly including 3-chloro-2,3,3-trifluoropropene and 2-chloro-3,3,3-trifluoropropene) column bottom liquid obtained from the third separation column 15 can be recycled to the second catalytic reactor 12 for further fluorination. In order to avoid accumulation of some chlorine-containing heavy column bottom liquid, part of the chlorine-containing heavy column bottom liquid can be removed regularly, and the removed materials can be subjected to intermittent rectification to further recover useful materials therefrom.

HCl, tail gas, and separated HF and $Cl_2$ in the present disclosure can be further recycled through a compressor.

The present disclosure is further described in detail below by means of embodiments, but the present disclosure is not limited to the embodiments described below.

The composite nanofiltration membrane used in the first membrane separator in the embodiments can be homemade and the preparation method of the composite nanofiltration membrane includes the following steps:

(1) placing 0.25 to 1 part of carbon nanotubes by weight into 100 parts of solvent N,N-dimethylformamide by weight, and carrying out ultrasonic dispersion for 4 h to 6 h to obtain a mixed solution;

(2) placing 30 to 60 parts of polyvinylidene fluoride by weight and 18 to 40 parts of polyimide by weight into the mixed solution obtained in step (1), and stirring the solution for 10 to 20 hours to obtain a casting solution;

(3) resting the casting solution, obtained in step (2), at 25° C. to 30° C. for 24 h to 48 h to obtain a degassed casting solution;

(4) scraping the degassed casting solution obtained in step (3) at 10° C. to 20° C. to obtain a scraped casting solution; and (5) volatilizing the scraped casting solution obtained in step (4) in the air for 1 min to 5 min, placing the volatilized casting solution in deionized water so that the casting solution is coagulated into a membrane, taking out the formed membrane from the coagulating solution, and rinsing the membrane with deionized water, thus obtaining the composite nanofiltration membrane.

The modified nanofiltration membrane used in the first membrane separator in the embodiments can be homemade and the preparation method of the composite nanofiltration membrane includes the following steps:

(1) cleaning a polyethersulfone base membrane with deionized water, and soaking the polyethersulfone base membrane in deionized water for 8 h to 12 h, and changing the deionized water every 2 h, thus obtaining the soaked polyethersulfone base membrane;

(2) placing the soaked polyethersulfone base membrane, obtained in step (1), in a polyacrylic acid solution with a concentration of 0.05 mol/L to 0.1 mol/L, the polyacrylic acid solution immersing the polyethersulfone base membrane for 2 cm to 5 cm, and bubbling with $N_2$ for 0.5 h to 1 h to remove oxygen out of the solution; and (3) under the protection of nitrogen at room temperature, using a low-voltage mercury lamp with a power of 400 W to 800 W to irradiate the solution obtained in step (2) for 50 min to 120 min, wherein the low-voltage mercury lamp was 20 cm to 40 cm away from the liquid surface; then, taking out the membrane, and rinsing the membrane with deionized water, thus obtaining the modified nanofiltration membrane.

The activation process of the first catalytic reactor before the reaction in the examples is as follows: slowly heating the first catalytic reactor filled with 300 m³ of a catalyst to 260° C. at a rate of 1° C./min, and introducing AHF diluted with nitrogen for activation for 12 h, where the flow rate of AHF is 25 g/h, and the flow rate of $N_2$ is 0.15 L/min. After the activation is completed, the temperature is adjusted to the reaction temperature for later use.

The activation process of the second catalytic reactor before the reaction in the embodiments is as follows: slowly heating the second catalytic reactor filled with 300 m³ of a catalyst to 280° C. at a rate of 1° C./min, and introducing AHF diluted with nitrogen for activation for 12 h, where the flow rate of AHF is 35 g/h, and the flow rate of $N_2$ is 0.2 L/min. After the activation is completed, the temperature is raised to the reaction temperature for later use.

Example 1

(1) The mass ratio of carbon tetrachloride to a composite catalyst was 49:1; the composite catalyst was composed of, by weight: 1.0 part of a co-catalyst tributyl phosphate and 1.0 part of a catalyst (200-mesh iron powder); the reaction temperature was 90° C., the molar ratio of carbon tetrachloride to ethylene was 1, the residence time is 120 min, and the system pressure was maintained at 1.0 Mpa; sampling analysis was carried out; calculated on the basis of ethylene, the conversion rate was 90%, and the HCC-250fb selectivity was 96.5%;

(2) the reaction product obtained in step (1) was introduced into a first membrane separator (with a membrane area of 0.4 m²) for separation through a pump at a flow rate of 70 ml/min to obtain a first stream (based on sampling analysis, including, by weight, 87 parts of carbon tetrachloride, 10 parts of HCC-250fb, 2.0 parts of tetrachloroethylene, and 1.0 part of hexachloroethane) and a second stream (based on sampling analysis, including, by weight, 90 parts of HCC-250fb, 1 part of a catalyst, 2.5 parts of a co-catalyst, 4.5 parts of carbon tetrachloride, 1.2 parts of hexachloroethane, and 0.8 parts of 1,1,1,5-tetrachloropentane), where the operating pressure of the first membrane separator was maintained at 0.5 Mpa and the operating temperature of the first membrane separator was maintained at 80° C.;

(3) the second stream was introduced into a second membrane separator (with a membrane area of 0.2 m²) for separation through a pump at a flow rate of 10 ml/min to obtain a third stream (based on sampling analysis, including, by weight, 86 parts of HCC-250fb, 10 parts of carbon tetrachloride, 2 parts of hexachloroethane, and 2.0 parts of the balance) and a fourth stream (based on sampling analysis, including, by weight, 5 parts of HCC-250fb, 5 parts of carbon tetrachloride, 2 parts of hexachloroethane, 1 part of 1,1,1,5-tetrachloropentane, 15 parts of a catalyst, and 72 parts of a co-catalyst), and recycling the fourth stream to a telomerization reactor, where the operating pressure of the second membrane separator was maintained at 1.5 Mpa and the operating temperature of the second membrane separator was maintained at 40° C.;

(4) the third stream was mixed with the first stream obtained in step (2) and then the mixture was introduced into a first separation column (packed column) to obtain an overhead fraction (mainly including carbon tetrachloride) of the first separation column and a bottom component of the first separation column (based on sampling analysis, including, by weight, 98 parts of HCC-250fb); the overhead fraction of the first separation column was recycled to the telomerization reactor;

(5) the bottom component of the first separation column was introduced in a first cracking reactor (tubular reactor, including a preheating zone (⅕), and a reaction zone (⅗), a cooling outlet zone (⅕), using molten salt bath for heating, a single tube with an inner diameter of 8 mm and a length of 35 cm, and a total of 20 single tubes) for high-temperature cracking, where the cracking temperature was 350° C., and the residence time was 1 s; and the cracking gas was condensed to separate the HCl tail gas, thus obtaining a second reaction product; based on sampling and analysis, the conversion rate of HCC-250fb was 90.0%, and the total selectivity of 1,1,3-trichloropropene/3,3,3-trichloropropene was 99%;

(6) the second reaction product and chlorine gas were introduced into a chlorination reactor (tubular reactor, including a preheating zone (⅕), a reaction zone (⅗), and a cooling outlet zone (⅕), using molten salt bath for heating, a single tube with an inner diameter of 6 mm and a length of 50 cm, and a total of 40 single tubes) for gas-phase chlorination, where the gas-phase chlorination temperature was 140° C., the residence time was 5.5 s, and the molar ratio of chlorine gas to the second reaction product was 1.0; the chlorination product was condensed to separate HCl tail gas, thus obtaining a third reaction product; based on sampling and analysis, the conversion rate of trichloropropene (1,1,3-trichloropropene/3,3,3-trichloropropene) was 99.7%, and the selectivity was 99.00%;

(7) the third reaction product was introduced in a second cracking reactor (tubular reactor, including a preheating zone (⅕), and a reaction zone (⅗), a cooling outlet zone (⅕), using molten salt bath for heating, a single tube with an inner diameter of 5 mm and a length of 45 cm, and a total of 30 single tubes) for high-temperature cracking, where the cracking temperature was 350° C., and the residence time was 15 s; and the cracking gas was condensed to separate the HCl tail gas, thus obtaining a fourth reaction product; based on sampling and analysis, the conversion rate was 54% and the selectivity was 97.6% (calculated based on HCC-240db);

(8) the fourth reaction product and hydrogen fluoride were introduced into a first catalytic reactor filled with 300 ml of a $Nd_2O_3$—$Cr_2O_3$ catalyst (including, by weight, 5 parts $Nd_2O_3$, 95 parts of $Cr_2O_3$) for gas-phase catalytic fluorination reaction to obtain a fifth reaction product, where the reaction was carried out at 300° C. under a pressure of 1.5 Mpa with a contact time of 1 s, and the molar ratio of HF to the fourth reaction product was 5; based on sampling gas chromatography analysis, it was observed that the total conversion rate of TCP and HCC-240db was 100% and the total selectivity of HFO-1233xf and HFO-1234yf was 95.3%; and (9) the fifth reaction product and hydrogen fluoride were introduced into a second catalytic reactor filled with 300 ml of a catalyst $Dy_2O_3$—$Tm_2O_3$—$Cr_2O_3$ (including, by weight, 5 parts of $Dy_2O_3$, 3 parts of $Tm_2O_3$, and 92 parts of $Cr_2O_3$) for gas-phase catalytic fluorination reaction to obtain a reaction product, where the reaction was carried out at 330° C. under a pressure of 1.2 Mpa with a contact time of 5 s, and the molar ratio of HF to the fourth reaction product was 30; and the reaction product was then condensed and rectified to obtain chlorine-containing heavy column bottom liquid and 2,3,3,3-tetrafluoropropene product. Based on sampling gas-chromatography analysis, it was observed that the conversion rate of HFO-1233xf was 95.0%, and the selectivity of HFO-1234yf was 96.1%.

Example 2

(1) The mass ratio of carbon tetrachloride to a composite catalyst was 63.5:1; the composite catalyst was composed of, by weight: 0.75 parts of a co-catalyst tributyl phosphate and 0.8 parts of a catalyst (200-mesh iron powder); the reaction temperature was 110° C., the molar ratio of carbon tetrachloride to ethylene was 2, the residence time was 90 min, and the system pressure was maintained at 0.7 Mpa; sampling analysis was carried out; calculated on the basis of ethylene, the conversion rate was 99%, and the HCC-250fb selectivity was 95.0%;

(2) the reaction product obtained in step (1) was introduced into a first membrane separator (with a membrane area of 0.4 m²) for separation to obtain a first stream (based on sampling analysis, including, by weight, 88 parts of carbon tetrachloride, 9 parts of HCC-250fb, 2.5 parts of tetrachloroethylene, and 0.5 parts of hexachloroethane) and a second stream (based on sampling analysis, including, by weight, 90.5 parts of HCC-250fb, 1 part of a catalyst, 3 parts of a co-catalyst, 4.0 parts of carbon tetrachloride, 1.0 part of hexachloroethane, and 0.5 parts of 1,1,1,5-tetrachloropentane), where the operating pressure of the first membrane separator was maintained at 0.8 Mpa and the operating temperature of the first membrane separator was maintained at 25° C.;

(3) the second stream was introduced into a second membrane separator (with a membrane area of 0.2 m²) for separation to obtain a third stream (based on sampling analysis, including, by weight, 89 parts of HCC-250fb, 7 parts of carbon tetrachloride, 2 parts of hexachloroethane, and 2 parts of the balance) and a fourth stream (based on sampling analysis, including, by weight, 6 parts of HCC-250fb, 3 parts of carbon tetrachloride, 2 parts of hexachloroethane, 2 parts of 1,1,1,2-tetrachloropentane, 14 parts of a catalyst, and 73 parts of a co-catalyst), and recycling the fourth stream to a telomerization reactor, where the operating pressure of the second membrane separator was maintained at 1.2 Mpa and the operating temperature of the second membrane separator was maintained at 40° C.;

(4) the third stream was mixed with the first stream obtained in step (2) and then the mixture was introduced into a first separation column (packed column) to obtain an overhead fraction (mainly including carbon tetrachloride) of the first separation column and a bottom component of the first separation column (based on sampling analysis, including, by weight, 98.5 parts of HCC-250fb); the overhead fraction of the first separation column was recycled to the telomerization reactor;

(5) the bottom component of the first separation column was introduced in a first cracking reactor (tubular reactor, including a preheating zone (⅕), and a reaction zone (⅗), a cooling outlet zone (⅕), using molten salt bath for heating, a single tube with an inner diameter of 8 mm and a length of 35 cm, and a total of 20 single tubes) for high-temperature cracking, where the cracking temperature was 450° C., and the residence time was 2 s; and the cracking gas was condensed to separate the HCl tail gas, thus obtaining a second reaction product; based on sampling and analysis, the conversion rate of HCC-250fb was 96%, and the total selectivity of 1,1,3-trichloropropene and 3,3,3-trichloropropene was 99.1%;

(6) the second reaction product and chlorine gas were introduced into a chlorination reactor (tubular reactor, including a preheating zone (⅕), a reaction zone (⅗), and a cooling outlet zone (⅕), using molten salt bath for heating, a single tube with an inner diameter of 6 mm and a length of 50 cm, and a total of 40 single tubes) for gas-phase chlorination, where the gas-phase chlorination temperature was 140° C., the residence time was 3 s, and the molar ratio of chlorine gas to the second reaction product was 4.0; the chlorination product was condensed to separate HCl tail gas, thus obtaining a third reaction product; based on sampling and analysis, the conversion rate of trichloropropene (1,1,3-trichloropropene/3,3,3-trichloropropene) was 99.8%, and the selectivity was 94.00%;

(7) the third reaction product was introduced in a second cracking reactor (tubular reactor, including a preheating zone (⅕), and a reaction zone (⅗), a cooling outlet zone (⅕), using molten salt bath for heating, a single tube with an inner diameter of 5 mm and a length of 45 cm, and a total of 30 single tubes) for high-temperature cracking, where the cracking temperature was 400° C., and the residence time was 10 s; and the cracking gas was condensed to separate the HCl tail gas, thus obtaining a fourth reaction product; based on sampling and analysis, the conversion rate was 50% and the selectivity was 98.4% (calculated based on HCC-240db);

(8) the fourth reaction product and hydrogen fluoride were introduced into a first catalytic reactor filled with 300 ml of a $Nd_2O_3$—$Cr_2O_3$ catalyst (including, by weight, 15 parts $Nd_2O_3$ and 85 parts of $Cr_2O_3$) for gas-phase catalytic fluorination reaction to obtain a fifth reaction product, where the reaction was carried out at 270° C. under a pressure of 1.0 Mpa with a contact time of 6 s, and the molar ratio of HF to the fourth reaction product was 25; based on sampling gas chromatography analysis, it was observed that the total conversion rate of TCP and HCC-240db was 100% and the total selectivity of HFO-1233xf and HFO-1234yf was 96.8%; and (9) the fifth reaction product and hydrogen fluoride were introduced into a second catalytic reactor filled with 300 ml of a catalyst $Dy_2O_3$—$Tm_2O_3$—$Cr_2O_3$ (including, by weight, 10 parts of $Dy_2O_3$, 10 parts of $Tm_2O_3$, and 80 parts of $Cr_2O_3$) for gas-phase catalytic fluorination reaction to obtain a reaction product, where the reaction was carried out at 300° C. under a pressure of 1.0 Mpa with a contact time of 10 s, and the molar ratio of HF to the fourth reaction product was 25; and the reaction product was then condensed and rectified to obtain chlorine-containing heavy column bottom liquid and 2,3,3,3-tetrafluoropropene product. Based on sampling gas-chromatography analysis, it was observed that the conversion rate of HFO-1233xf was 98.4%, and the selectivity of HFO-1234yf was 95.7%.

Example 3

(1) The mass ratio of carbon tetrachloride to a composite catalyst was 99:1; the composite catalyst was composed of, by weight: 0.5 parts of a co-catalyst tributyl phosphate and 0.5 parts of a catalyst (200-mesh iron powder); the reaction temperature was 120° C., the molar ratio of carbon tetrachloride to ethylene was 4, the residence time was 60 min, and the reaction pressure was maintained at 0.5 Mpa; sampling analysis was carried out; calculated on the basis of ethylene, the conversion rate was 99%, and the HCC-250fb selectivity was 95.0%;

(2) the reaction product obtained in step (1) was introduced into a first membrane separator (with a membrane area of 0.4 m²) for separation through a pump at a flow rate of 10 ml/min to obtain a first stream (based on sampling analysis, including, by weight, 89 parts of carbon tetrachloride, 8 parts of HCC-250fb, 2.5 parts of tetrachloroethylene, and 0.5 parts of hexachloroethane) and a second stream (based on sampling analysis, including, by weight, 88 parts of HCC-250fb, 2 parts of a catalyst, 3.0 parts of a co-catalyst, 5 parts of carbon tetrachloride, 1.2 parts of hexachloroethane, and 0.8 parts of 1,1,1,5-tetrachloropentane), where the operating pressure of the first membrane separator was maintained at 1.0 Mpa and the operating temperature of the first membrane separator was maintained at 15° C.;

(3) the second stream was introduced into a second membrane separator (with a membrane area of 0.2 m²) for separation through a pump at a flow rate of 40 ml/min to obtain a third stream (based on sampling analysis, including, by weight, 90 parts of HCC-250fb, 5 parts of carbon tetrachloride, 2 parts of hexachloroethane, and 3.0 parts of the balance) and a fourth stream (based on sampling analysis, including, by weight, 6 parts of HCC-250fb, 2 parts of carbon tetrachloride, 1.5 parts of hexachloroethane, 1.5 part of 1,1,1,2-tetrachloropentane, 11 parts of a catalyst, and 78 parts of a co-catalyst), and recycling the fourth stream to a telomerization reactor, where the operating pressure of the second membrane separator was maintained at 1.2 Mpa and the operating temperature of the second membrane separator was maintained at 60° C.;

(4) the third stream was mixed with the first stream obtained in step (2) and then the mixture was introduced into a first separation column (packed column) to obtain an overhead fraction (mainly including carbon tetrachloride) of the first separation column and a bottom component of the first separation column (based on sampling analysis, including, by weight, 98.7 parts of HCC-250fb); the overhead fraction of the first separation column was recycled to the telomerization reactor;

(5) the bottom component of the first separation column was introduced in a first cracking reactor (tubular reactor, including a preheating zone (⅕), and a reaction zone (⅗), a cooling outlet zone (⅕), using molten salt bath for heating, a single tube with an inner diameter of 8 mm and a length of 35 cm, and a total of 20 single tubes) for high-temperature cracking, where the cracking temperature was 500° C., and the residence time was 5 s; and the cracking gas was condensed to separate the HCl tail gas, thus obtaining a second reaction product; based on sampling and analysis, the conversion rate of HCC-250fb was 98%, and the total selectivity of 1,1,3-trichloropropene and 3,3,3-trichloropropene was 97%;

(6) the second reaction product and chlorine gas were introduced into a chlorination reactor (tubular reactor, including a preheating zone (⅕), a reaction zone (⅗), and a cooling outlet zone (⅕), using molten salt bath for heating, a single tube with an inner diameter of 6 mm and a length of 50 cm, and a total of 40 single tubes) for gas-phase chlorination, where the gas-phase chlorination temperature was 160° C., the residence time was is, and the molar ratio of chlorine gas to the second reaction product was 2.0; the chlorination product was condensed to separate HCl tail gas, thus obtaining a third reaction product; based on sampling and analysis, the conversion rate of trichloropropene (1,1,3-trichloropropene/3,3,3-trichloropropene) was 99.1%, and the selectivity was 98.00%;

(7) the third reaction product was introduced in a second cracking reactor (tubular reactor, including a preheating zone (⅕), and a reaction zone (⅗), a cooling outlet zone (⅕), using molten salt bath for heating, a single tube with an inner diameter of 5 mm and a length of 45 cm, and a total of 30 single tubes) for high-temperature cracking, where the cracking temperature was 500° C., and the residence time was 2 s; and the cracking gas was condensed to separate the HCl tail gas, thus obtaining a fourth reaction product; based on sampling and analysis, the conversion rate was 70% and the selectivity was 97.1% (calculated based on HCC-240db);

(8) the fourth reaction product and hydrogen fluoride were introduced into a first catalytic reactor filled with 300 ml of a $Nd_2O_3$—$Cr_2O_3$ catalyst (including, by weight, 25 parts $Nd_2O_3$ and 75 parts of $Cr_2O_3$) for gas-phase catalytic fluorination reaction to obtain a fifth reaction product, where the reaction was carried out at 250° C. under a pressure of 0.8 Mpa with a contact time of 25 s, and the molar ratio of HF to the fourth reaction product was 15; based on sampling gas chromatography analysis, it was observed that the total conversion rate of TCP and HCC-240db was 100% and the total selectivity of HFO-1233xf and HFO-1234yf was 96.1%; and (9) the fifth reaction product and hydrogen fluoride were introduced into a second catalytic reactor filled with 300 ml of a catalyst $Dy_2O_3$—$Tm_2O_3$—$Cr_2O_3$ (including, by weight, 15 parts of $Dy_2O_3$, 5 parts of $Tm_2O_3$, and 80 parts of $Cr_2O_3$) for gas-phase catalytic fluorination reaction to obtain a reaction product, where the reaction was carried out at 280° C. under a pressure of 0.8 Mpa with a contact time of 15 s, and the molar ratio of HF to the fourth reaction product was 5; and the reaction product was then condensed and rectified to obtain chlorine-containing heavy column bottom liquid and 2,3,3,3-tetrafluoropropene product. Based on sampling gas-chromatography analysis, it was observed that the conversion rate of HFO-1233xf was 97.6%, and the selectivity of HFO-1234yf was 95.9%.

Example 4

(1) The mass ratio of carbon tetrachloride to a composite catalyst was 54.5:1; the composite catalyst was composed of, by weight: 1.0 part of a co-catalyst tributyl phosphate and 0.8 parts of a catalyst (200-mesh iron powder); the reaction temperature was 110° C., the molar ratio of carbon tetrachloride to ethylene was 2, the residence time was 90 min, and the system pressure was maintained at 0.7 Mpa; sampling analysis was carried out; calculated on the basis of ethylene, the conversion rate was 99%, and the HCC-250fb selectivity was 98.1%;

(2) the reaction product obtained in step (1) was introduced into a first membrane separator (with a membrane area of 0.4 $m^2$) for separation through a pump at a flow rate of 40 ml/min to obtain a first stream (based on sampling analysis, including, by weight, 90 parts of carbon tetrachloride, 6 parts of HCC-250fb, 3 parts of tetrachloroethylene, and 1 part of hexachloroethane) and a second stream (based on sampling analysis, including, by weight, 93 parts of HCC-250fb, 1 part of a catalyst, 2.5 parts of a co-catalyst, 1.5 parts of carbon tetrachloride, 1.2 parts of hexachloroethane, and 0.8 parts of 1,1,1,5-tetrachloropentane), where the operating pressure of the first membrane separator was maintained at 0.8 Mpa and the operating temperature of the first membrane separator was maintained at 25° C.;

(3) the second stream was introduced into a second membrane separator (with a membrane area of 0.2 $m^2$) for separation through a pump at a flow rate of 20 ml/min to obtain a third stream (based on sampling analysis, including, by weight, HCC-250fb, 2 parts of carbon tetrachloride, 1.5 parts of hexachloroethane, and 1.5 parts of the balance) and a fourth stream (based on sampling analysis, including, by weight, 5 parts of HCC-250fb, 3 parts of carbon tetrachloride, 2 parts of hexachloroethane, 1 part of 1,1,1,0-tetrachloropentane, 18 parts of a catalyst, and 71 parts of a co-catalyst), and recycling the fourth stream to a telomerization reactor, where the operating pressure of the second membrane separator was maintained at 1.0 Mpa and the operating temperature of the second membrane separator was maintained at 25° C.;

(4) the third stream was mixed with the first stream obtained in step (2) and then the mixture was introduced into a first separation column (packed column) to obtain an overhead fraction (mainly including carbon tetrachloride) of the first separation column and a bottom component of the first separation column (based on sampling analysis, including, by weight, 99 parts of HCC-250fb); the overhead fraction of the first separation column was recycled to the telomerization reactor;

(5) the bottom component of the first separation column was introduced in a first cracking reactor (tubular reactor, including a preheating zone (⅕), and a reaction zone (⅗), a cooling outlet zone (⅕), using molten salt bath for heating, a single tube with an inner diameter of 8 mm and a length of 35 cm, and a total of 20 single tubes) for high-temperature cracking, where the cracking temperature was 450° C., and the residence time was 8 s; and the cracking gas was condensed to separate the HCl tail gas, thus obtaining a second reaction product; based on sampling and analysis, the conversion rate of HCC-250fb was 99%, and the total selectivity of 1,1,3-trichloropropene and 3,3,3-trichloropropene was 96%;

(6) the second reaction product and chlorine gas were introduced into a chlorination reactor (tubular reactor, including a preheating zone (⅕), a reaction zone (⅗), and a cooling outlet zone (⅕), using molten salt bath for heating, a single tube with an inner diameter of 6 mm and a length of 50 cm, and a total of 40 single tubes) for gas-phase chlorination, where the gas-phase chlorination temperature was 170° C., the residence time was 0.8 s, and the molar ratio of chlorine gas to the second reaction product was 3.0; the chlorination product was condensed to separate HCl tail gas, thus obtaining a third reaction product; based on sampling and analysis, the conversion rate of trichloropropene (1,1,3-trichloropropene/3,3,3-trichloropropene) was 98.8%, and the selectivity was 99.3%;

(7) the third reaction product was introduced in a second cracking reactor (tubular reactor, including a preheating zone (⅕), and a reaction zone (⅗), a cooling outlet zone (⅕), using molten salt bath for heating, a single tube with an inner diameter of 5 mm and a length of 45 cm, and a total of 30 single tubes) for high-temperature cracking, where the cracking temperature was 450° C., and the residence time was 8 s; and the cracking gas was condensed to separate the HCl tail gas, thus obtaining a fourth reaction product; based on sampling and analysis, the conversion rate was 64% and the selectivity was 98.4% (calculated based on HCC-240db);

(8) the fourth reaction product and hydrogen fluoride were introduced into a first catalytic reactor filled with 300 ml of a $Nd_2O_3$—$Cr_2O_3$ catalyst (including, by weight, 25 parts $Nd_2O_3$ and 75 parts of $Cr_2O_3$) for gas-phase catalytic fluorination reaction to obtain a fifth reaction product, where the reaction was carried out at 250° C. under a pressure of 0.9 Mpa with a contact time of 8 s, and the molar ratio of HF to the fourth reaction product was 10; based on sampling gas chromatography analysis, it was observed that the total conversion rate of TCP and HCC-240db was 100% and the total selectivity of HFO-1233xf and HFO-1234yf was 97.1%; and (9) the fifth reaction product and hydrogen fluoride were introduced into a second catalytic reactor filled with 300 ml of a catalyst $Dy_2O_3$—$Tm_2O_3$—$Cr_2O_3$ (including, by weight, 15 parts of $Dy_2O_3$, 5 parts of $Tm_2O_3$, and 80 parts of $Cr_2O_3$) for gas-phase catalytic fluorination reaction to obtain a reaction product, where the reaction was carried out at 300° C. under a pressure of 0.8 Mpa with a contact time of 35 s, and the molar ratio of HF to the fourth reaction product was 15; and the reaction product was then condensed and rectified to obtain chlorine-containing heavy column bottom liquid and 2,3,3,3-tetrafluoropropene product. Based on sampling gas-chromatography analysis, it was observed that the conversion rate of HFO-1233xf was 98.9%, and the selectivity of HFO-1234yf was 96.8%.

Example 5

(1) The mass ratio of carbon tetrachloride to a composite catalyst was 76:1; the composite catalyst was composed of, by weight: 0.8 parts of a co-catalyst tributyl phosphate and 0.5 parts of a catalyst (200-mesh iron powder); the reaction temperature was 100° C., the molar ratio of carbon tetrachloride to ethylene was 2, the residence time was 90 min, and the system pressure was maintained at 1.0 Mpa; sampling analysis was carried out; calculated on the basis of ethylene, the conversion rate was 99%, and the HCC-250fb selectivity was 95.0%;

(2) the reaction product obtained in step (1) was introduced into a first membrane separator (with a membrane area of 0.4 $m^2$) for separation through a pump at a flow rate of 40 ml/min to obtain a first stream (based on sampling analysis, including, by weight, 90 parts of carbon tetrachloride, 8 parts of HCC-250fb, 1.5 parts of tetrachloroethylene, and 0.5 parts of hexachloroethane) and a second stream (based on sampling analysis, including, by weight, 92 parts of HCC-250fb, 2 parts of a catalyst, 2.5 parts of a co-catalyst, 1.5 parts of carbon tetrachloride, 1.0 part of hexachloroethane, and 1.0 part of 1,1,1,5-tetrachloropentane), where the operating pressure of the first membrane separator was maintained at 0.8 Mpa and the operating temperature of the first membrane separator was maintained at 30° C.;

(3) the second stream was introduced into a second membrane separator (with a membrane area of 0.2 $m^2$) for separation through a pump at a flow rate of 20 ml/min to obtain a third stream (based on sampling analysis, including, by weight, 92 parts of HCC-250fb, 7 parts of carbon tetrachloride, 0.5 parts of hexachloroethane, and 0.5 parts of the balance) and a fourth stream (based on sampling analysis, including, by weight, 5 parts of HCC-250fb, 4 parts of carbon tetrachloride, 2 parts of hexachloroethane, 3 parts of 1,1,1,1-tetrachloropentane, 11 parts of a catalyst, and 75 parts of a co-catalyst), and recycling the fourth stream to a telomerization reactor, where the operating pressure of the second membrane separator was maintained at 1.1 Mpa and the operating temperature of the second membrane separator was maintained at 30° C.;

(4) the third stream was mixed with the first stream obtained in step (2) and then the mixture was introduced into a first separation column (packed column) to obtain an overhead fraction (mainly including carbon tetrachloride) of the first separation column and a bottom component of the first separation column (based on sampling analysis, including, by weight, 99.6 parts of HCC-250fb); the overhead fraction of the first separation column was recycled to the telomerization reactor;

(5) the bottom component of the first separation column was introduced in a first cracking reactor (tubular reactor, including a preheating zone (⅕), and a reaction zone (⅗), a cooling outlet zone (⅕), using molten salt bath for heating, a single tube with an inner diameter of 8 mm and a length of 35 cm, and a total of 20 single tubes) for high-temperature cracking, where the cracking temperature was 450° C., and the residence time was 3 s; and the cracking gas was condensed to separate the HCl tail gas, thus obtaining a second reaction product; based on sampling and analysis, the conversion rate of HCC-250fb was 97%, and the total selectivity of 1,1,3-trichloropropene and 3,3,3-trichloropropene was 99%;

(6) the second reaction product and chlorine gas were introduced into a chlorination reactor (tubular reactor, including a preheating zone (⅕), a reaction zone (⅗), and a cooling outlet zone (⅕), using molten salt bath for heating, a single tube with an inner diameter of 6 mm and a length of 50 cm, and a total of 40 single tubes) for gas-phase chlorination, where the gas-phase chlorination temperature was 140° C., the residence time was 0.8 s, and the molar ratio of chlorine gas to the second reaction product was 1.2; the chlorination product was condensed to separate HCl tail gas, thus obtaining a third reaction product; based on sampling and analysis, the conversion rate of trichloropropene (1,1,3-trichloropropene/3,3,3-trichloropropene) was 99.4%, and the selectivity was 99.6%;

(7) the third reaction product was introduced in a second cracking reactor (tubular reactor, including a preheating zone (⅕), and a reaction zone (⅗), a cooling outlet zone (⅕), using molten salt bath for heating, a single tube with an inner diameter of 5 mm and a length of 45 cm, and a total of 30 single tubes) for high-temperature cracking, where the cracking temperature was 430° C., and the residence time was 5 s; and the cracking gas was condensed to separate the HCl tail gas, thus obtaining a fourth reaction product; based on sampling and analysis, the conversion rate was 58% and the selectivity was 98.8% (calculated based on HCC-240db);

(8) the fourth reaction product and hydrogen fluoride were introduced into a first catalytic reactor filled with 300 ml of a $Nd_2O_3$—$Cr_2O_3$ catalyst (including, by weight, 20 parts $Nd_2O_3$ and 80 parts of $Cr_2O_3$) for gas-phase catalytic fluorination reaction to obtain a fifth reaction product, where the reaction was carried out at 250° C. under a pressure of 0.7 Mpa with a contact time of 10 s, and the molar ratio of HF to the fourth reaction product was 13; based on sampling gas chromatography analysis, it was observed that the total conversion rate of TCP and HCC-240db was 100% and the total selectivity of HFO-1233xf and HFO-1234yf was 98.4%; and (9) the fifth reaction product and hydrogen fluoride were introduced into a second catalytic reactor filled with 300 ml of a catalyst $Dy_2O_3$—$Tm_2O_3$—$Cr_2O_3$ (including, by weight, 10 parts of $Dy_2O_3$, 15 parts of $Tm_2O_3$, and 75 parts of $Cr_2O_3$) for gas-phase catalytic fluorination reaction to obtain a reaction product, where the reaction was carried out at 260° C. under a pressure of 1.2 Mpa with a contact time of 12 s, and the molar ratio of HF to the fourth reaction product was 20; and the reaction product was then condensed and rectified to obtain chlorine-containing heavy column bottom liquid and 2,3,3,3-tetrafluoropropene product. Based on sampling gas-chromatography analysis, it was observed that the conversion rate of HFO-1233xf was 99.0%, and the selectivity of HFO-1234yf was 97.1%.

What is claimed is:

1. A continuous preparation method of 2,3,3,3-tetrafluoropropene, comprising the following steps:
    step 1, in the presence of a composite catalyst, continuously introducing ethylene and carbon tetrachloride into a telomerization reactor for liquid-phase catalytic telomerization reaction to obtain a first reaction product, wherein the reaction is carried out at a temperature of 90° C. to 120° C., under a pressure of 0.5 Mpa to 1.0 Mpa and with a residence time of 1 h to 2 h, a molar ratio of carbon tetrachloride to ethylene is (1-4):1, and a mass ratio of carbon tetrachloride to composite catalyst is (40-100):1;
    step 2, introducing the first reaction product obtained in the step 1 into a first membrane separator for separation to obtain a first stream and a second stream;
    step 3, introducing the second stream obtained in the step 2 into a second membrane separator for separation to obtain a third stream and a fourth stream, and recycling the fourth stream to the telomerization reactor;
    step 4, mixing the third stream obtained in the step 3 with the first stream obtained in the step 2, and then introducing the mixture into a first separation column to obtain an overhead fraction of the first separation column and a bottom component of the first separation column, and recycling the overhead fraction of the first separation column to the telomerization reactor;
    step 5, carrying out high-temperature cracking and condensing on the bottom component of the first separation column obtained in the step 4 to obtain a second reaction product, wherein the cracking is carried out at a temperature of 350° C. to 500° C., and the residence time is within a range of 1 s to 8 s;
    step 6, carrying out gas-phase chlorination and condensing on the second reaction product obtained in the step 5 in the presence of chlorine gas to obtain a third reaction product, wherein the gas-phase chlorination is carried out at a temperature of 140° C. to 170° C., the residence time is within a range of 0.5 s to 5.5 s, and a molar ratio of the chlorine gas to the second reaction product is (1.0-4):1;
    step 7, carrying out high-temperature cracking and condensing on the third reaction product obtained in the step 6 to obtain a fourth reaction product, wherein the cracking is carried out at a temperature of 350° C. to 500° C., and the residence time is within a range of 2 s to 15 s;
    step 8, in the presence of a first fluorination catalyst, introducing the fourth reaction product obtained in the step 7 and hydrogen fluoride into a first catalytic reactor for gas-phase catalytic fluorination reaction to obtain a fifth reaction product, wherein the reaction is carried out at a temperature of 250° C. to 300° C., under a pressure of 0.5 Mpa to 1.5 Mpa, with a contact time of 1 s to 25 s, and a molar ratio of the HF to the fourth reaction product is (5-25):1; and
    step 9, in the presence of a second fluorination catalyst, introducing the fifth reaction product obtained in the step 8 and hydrogen fluoride into a second catalytic reactor for gas-phase catalytic fluorination reaction, wherein the reaction is carried out at a temperature of 250° C. to 330° C., under a pressure of 0.8 Mpa to 1.2 Mpa, with a contact time of 5 s to 35 s, and a molar ratio of the HF to the fifth reaction product is (5-30):1; and condensing and rectifying the reaction product to obtain chlorine-containing column bottom liquid and a 2,3,3,3-tetrafluoropropene product.

2. The continuous preparation method of 2,3,3,3-tetrafluoropropene according to claim 1, wherein the composite catalyst in the step 1 comprises a catalyst and a co-catalyst, and comprises, by weight, 0.5 to 1 part of the catalyst and 0.5 to 1 part of the co-catalyst.

3. The continuous preparation method of 2,3,3,3-tetrafluoropropene according to claim 2, wherein the catalyst comprises one or more of iron powder, iron wires, ferric chloride, and ferrous chloride, and the co-catalyst is triethyl phosphate or tributyl phosphate.

4. The continuous preparation method of 2,3,3,3-tetrafluoropropene according to claim 1, wherein the first fluorination catalyst in the step 8 comprises, by weight, 5 to 25 parts of $Nd_2O_3$ and 75 to 95 parts of $Cr_2O_3$.

5. The continuous preparation method of 2,3,3,3-tetrafluoropropene according to claim 1, wherein the second fluorination catalyst in the step 9 comprises, by weight, 5 to 15 parts of $Dy_2O_3$, 3 to 20 parts of $Tm_2O_3$ and 60 to 94 parts of $Cr_2O_3$.

6. The continuous preparation method of 2,3,3,3-tetrafluoropropene according to claim 1, wherein the chlorine-containing column bottom liquid in the step 9 is recycled to the second catalytic reactor.

7. The continuous preparation method of 2,3,3,3-tetrafluoropropene according to claim 1, wherein in the step 2, the operating temperature of the first membrane separator is within a range of 15° C. to 80° C., and the operating pressure of the first membrane separator is within a range of 0.5 Mpa to 1.0 Mpa.

8. The continuous preparation method of 2,3,3,3-tetrafluoropropene according to claim 1, wherein in the step 3, the operating temperature of the second membrane separator is within a range of 25° C. to 60° C., and the operating pressure of the second membrane separator is within a range of 1.0 Mpa to 1.5 Mpa.

9. The continuous preparation method of 2,3,3,3-tetrafluoropropene according to claim 1, wherein a membrane used in the first membrane separator is a composite nanofiltration membrane, and a preparation method of the membrane comprises the following steps:

step a, placing 0.25 to 1 part of carbon nanotubes by weight into 100 parts of solvent N,N-dimethylformamide by weight, and carrying out ultrasonic dispersion for 4 h to 6 h to obtain a mixed solution;

step b, placing 30 to 60 parts of polyvinylidene fluoride by weight and 18 to 40 parts of polyimide by weight into the mixed solution obtained in the step a, and stirring the solution for 10 h to 20 h to obtain a casting solution;

step c, resting the casting solution, obtained in the step b, at 25° C. to 30° C. for 24 h to 48 h to obtain a degassed casting solution;

step d, scraping the degassed casting solution obtained in the step c at 10° C. to 20° C. to obtain a scraped casting solution; and step e, volatilizing the scraped casting solution, obtained in the step d, in the air for 1 min to 5 min, placing the volatilized casting solution in deionized water so that the casting solution is coagulated into a membrane, taking out the formed membrane from the coagulating solution, and rinsing the membrane with deionized water, thus obtaining the composite nanofiltration membrane.

10. The continuous preparation method of 2,3,3,3-tetrafluoropropene according to claim 3, wherein a membrane used in the second membrane separator is a modified nanofiltration membrane, and a preparation method of the membrane comprises the following steps:

step a', cleaning a polyethersulfone base membrane with deionized water, and soaking the polyethersulfone base membrane in deionized water for 8 h to 12 h, and changing the deionized water every 2 h, thus obtaining the soaked polyethersulfone base membrane;

step b', placing the soaked polyethersulfone base membrane, obtained in the step a', in a polyacrylic acid solution with a concentration of 0.05 to 0.1 mol/L, the polyacrylic acid solution immersing the polyethersulfone base membrane for 2 cm to 5 cm, and bubbling with $N_2$ for 0.5 h to 1h to remove oxygen out of the solution; and step c', under the protection of nitrogen at room temperature, using a low-pressure mercury lamp with a power of 400 W to 800 W to irradiate the solution obtained in the step b' for 50 min to 120 min, and then taking out the membrane, and rinsing the membrane with deionized water, thus obtaining the modified nanofiltration membrane.

* * * * *